(12) United States Patent
Schmidt et al.

(10) Patent No.: US 11,738,105 B2
(45) Date of Patent: Aug. 29, 2023

(54) DEVICES, SYSTEMS AND METHODS FOR TREATING MULTIPLE MEDICAL DEVICES HAVING PASSAGEWAYS WITH OZONE GAS

(71) Applicant: SoClean, Inc., Peterborough, NH (US)

(72) Inventors: Michael U. Schmidt, Franklin, MA (US); William E. Olszta, Webster, MA (US); Timothy Leyva, Bellingham, MA (US)

(73) Assignee: SOCLEAN, INC., Peterborough, NH (US)

( * ) Notice: Subject to any disclaimer, the term of this patent is extended or adjusted under 35 U.S.C. 154(b) by 1039 days.

(21) Appl. No.: 16/190,899

(22) Filed: Nov. 14, 2018

(65) Prior Publication Data

US 2019/0083668 A1 Mar. 21, 2019

Related U.S. Application Data

(63) Continuation of application No. 15/141,152, filed on Apr. 28, 2016, now Pat. No. 10,485,888, which is a
(Continued)

(51) Int. Cl.
*A61L 2/20* (2006.01)
*A61L 2/26* (2006.01)
(Continued)

(52) U.S. Cl.
CPC ............. *A61L 2/202* (2013.01); *A61L 2/10* (2013.01); *A61L 2/26* (2013.01); *A61L 2202/24* (2013.01);
(Continued)

(58) Field of Classification Search
CPC ....................................................... A61L 2/202
See application file for complete search history.

(56) References Cited

U.S. PATENT DOCUMENTS

| 4,019,986 A | 4/1977 | Burris et al. |
| 4,035,657 A | 7/1977 | Carlson |

(Continued)

FOREIGN PATENT DOCUMENTS

| CN | 1377708 | 11/2002 |
| CN | 2710637 | 7/2005 |

(Continued)

OTHER PUBLICATIONS

Office Action dated Jul. 29, 2019, issued in Chinese Patent Application No. 2017101786091, 10 pages.
(Continued)

*Primary Examiner* — Donald R Spamer
(74) *Attorney, Agent, or Firm* — Grossman, Tucker, Perreault & Pfleger, PLLC

(57) ABSTRACT

The present disclosure is generally related to systems, methods and devices for providing ozone treatment of multiple medical devices including passageways. In particular the systems, methods and devices may attach to multiple medical devices and clean, disinfect and/or sterilize the inner space of the tubes, including the areas most prone for bacteria buildup. A multi-channel ozone treatment device has an ozone operating system and a distribution line that splits into a plurality of distribution channels to distribute ozone to a plurality of ozone ports in a gas-tight compartment. A multi-port connector unit for connecting to a plurality of passageways in the gas-tight compartment is further disclosed.

9 Claims, 11 Drawing Sheets

Related U.S. Application Data continuation-in-part of application No. PCT/US2015/029418, filed on May 6, 2015, and a continuation-in-part of application No. 14/232,773, filed as application No. PCT/US2012/046593 on Jul. 13, 2012, now Pat. No. 9,358,316.

(60) Provisional application No. 61/508,341, filed on Jul. 15, 2011.

(51) Int. Cl.
*A61L 2/10* (2006.01)
*A61M 16/16* (2006.01)
*A61M 16/08* (2006.01)
*A61M 16/00* (2006.01)
*A61M 16/06* (2006.01)

(52) U.S. Cl.
CPC ............ *A61M 16/00* (2013.01); *A61M 16/06* (2013.01); *A61M 16/0875* (2013.01); *A61M 16/16* (2013.01); *A61M 2202/0216* (2013.01); *A61M 2205/502* (2013.01); *A61M 2205/581* (2013.01); *A61M 2205/583* (2013.01); *A61M 2205/584* (2013.01); *A61M 2209/10* (2013.01)

(56) References Cited

U.S. PATENT DOCUMENTS

| | | |
|---|---|---|
| 4,110,419 A | 8/1978 | Miller |
| 4,207,291 A | 6/1980 | Byrd et al. |
| 4,465,522 A | 8/1984 | Faldo et al. |
| 4,517,159 A | 5/1985 | Karlson |
| D295,074 S | 4/1988 | Jerge et al. |
| 4,743,275 A | 5/1988 | Flanagan |
| 4,787,980 A | 11/1988 | Ackermann et al. |
| 5,029,879 A | 7/1991 | Strang, Sr. et al. |
| 5,207,237 A | 5/1993 | Langford |
| 5,344,622 A | 9/1994 | Faddis et al. |
| 5,508,006 A | 4/1996 | Gabele et al. |
| 5,520,893 A | 5/1996 | Kasting, Jr. et al. |
| D371,203 S | 6/1996 | Deeds |
| D390,645 S | 2/1998 | Hanrahan et al. |
| 5,761,069 A | 6/1998 | Weber et al. |
| 5,787,537 A | 8/1998 | Mannillo |
| 5,920,075 A | 7/1999 | Whitehead |
| 6,024,066 A | 2/2000 | Nakayama et al. |
| 6,158,784 A | 12/2000 | Lavender |
| 6,276,304 B1 | 8/2001 | Tai |
| 6,280,633 B1 | 8/2001 | Conrad et al. |
| 6,379,617 B1 | 4/2002 | Spickermann |
| 6,379,632 B1 | 4/2002 | Kinoshita et al. |
| D476,423 S | 6/2003 | Picot et al. |
| 6,576,190 B1 | 6/2003 | Park |
| 6,605,260 B1 | 8/2003 | Busted |
| D487,315 S | 3/2004 | Picot et al. |
| 6,752,151 B2 | 6/2004 | Hill |
| 7,022,225 B1 | 4/2006 | Clawson et al. |
| 7,520,910 B2 | 4/2009 | Tilley |
| 7,527,603 B2 | 5/2009 | An |
| 7,676,276 B2 | 3/2010 | Karell |
| 7,767,168 B2 | 8/2010 | Namespetra et al. |
| 7,794,522 B2 | 9/2010 | Bliss et al. |
| 7,845,350 B1 | 12/2010 | Kayyali et al. |
| 8,051,853 B2 | 11/2011 | Berthon-Jones |
| 8,146,946 B1 | 4/2012 | Emond |
| 8,176,771 B2 | 5/2012 | Onishi et al. |
| 8,431,076 B2 | 4/2013 | Fraundorfer |
| D692,155 S | 10/2013 | Matoba et al. |
| 8,770,198 B2 | 7/2014 | Yee et al. |
| 8,815,164 B1 | 8/2014 | Al Azemi |
| D719,673 S | 12/2014 | Leyva et al. |
| D719,674 S | 12/2014 | Leyva et al. |
| 8,915,380 B2 | 12/2014 | Sowerby et al. |
| 9,022,247 B2 | 5/2015 | Enigmann |
| D733,315 S | 6/2015 | Lui |
| D733,316 S | 6/2015 | Lui |
| D748,280 S | 1/2016 | Lui |
| 9,358,316 B2 | 6/2016 | Leyva |
| D761,142 S | 7/2016 | Golta et al. |
| D776,290 S | 1/2017 | Wan et al. |
| 9,610,373 B2 | 4/2017 | Leyva |
| 9,616,147 B2 | 4/2017 | Leyva |
| 9,669,124 B2 | 6/2017 | Leyva et al. |
| D802,788 S | 11/2017 | Cormier et al. |
| 9,895,461 B2 | 2/2018 | Leyva et al. |
| 9,907,872 B2 | 3/2018 | Schmidt et al. |
| D819,190 S | 5/2018 | Cormier et al. |
| 10,052,397 B2 | 8/2018 | Leyva |
| 10,232,072 B2 | 3/2019 | Leyva et al. |
| 10,264,913 B2 | 4/2019 | Leyva |
| 10,398,797 B2 | 9/2019 | Leyva |
| 10,427,961 B2 | 10/2019 | Leyva et al. |
| 10,434,204 B2 | 10/2019 | Leyva et al. |
| 10,434,205 B2 | 10/2019 | Leyva |
| 10,456,492 B2 | 10/2019 | Leyva |
| 10,485,888 B2 | 11/2019 | Schmidt et al. |
| 2003/0000966 A1 | 1/2003 | Shelton |
| 2003/0063997 A1 | 4/2003 | Fryer et al. |
| 2003/0065292 A1 | 4/2003 | Darouiche et al. |
| 2003/0065297 A1 | 4/2003 | Davis et al. |
| 2003/0071069 A1 | 4/2003 | Shelton |
| 2004/0251125 A1 | 12/2004 | Yu |
| 2005/0017380 A1 | 1/2005 | Namespetra et al. |
| 2005/0019237 A1 | 1/2005 | Riley |
| 2005/0031486 A1* | 2/2005 | Mole .................. A61L 2/24 422/62 |
| 2005/0186108 A1 | 8/2005 | Fields |
| 2005/0220665 A1 | 10/2005 | Ding |
| 2006/0130834 A1 | 6/2006 | Chen |
| 2006/0272682 A1 | 12/2006 | Langford |
| 2007/0031778 A1 | 2/2007 | Helfenbein et al. |
| 2007/0065335 A1 | 3/2007 | Bedard et al. |
| 2008/0050290 A1 | 2/2008 | Yui |
| 2009/0267242 A1 | 10/2009 | Nichols et al. |
| 2010/0111792 A1 | 5/2010 | Nelson |
| 2010/0112677 A1 | 5/2010 | Onishi et al. |
| 2010/0147302 A1 | 6/2010 | Selvarajan et al. |
| 2012/0164025 A1 | 6/2012 | Stockley, III et al. |
| 2012/0227745 A1 | 9/2012 | Arcilia et al. |
| 2013/0017747 A1 | 1/2013 | Giloh |
| 2013/0239994 A1 | 9/2013 | Przyjemski |
| 2014/0154134 A1 | 6/2014 | Leyva |
| 2015/0004061 A1 | 1/2015 | Kain et al. |
| 2016/0235875 A1 | 8/2016 | Schmidt et al. |
| 2017/0165443 A1 | 6/2017 | Leyva |
| 2017/0202990 A1 | 7/2017 | Leyva |
| 2017/0209610 A1 | 7/2017 | Leyva et al. |
| 2017/0224857 A1 | 8/2017 | Leyva et al. |
| 2017/0225985 A1 | 8/2017 | Leyva et al. |
| 2018/0161466 A1 | 6/2018 | Schmidt et al. |
| 2019/0076561 A1 | 3/2019 | Leyva et al. |
| 2019/0076562 A1 | 3/2019 | Schmidt et al. |
| 2019/0151487 A1 | 5/2019 | Leyva |
| 2019/0167828 A1 | 6/2019 | Leyva |
| 2019/0388575 A1 | 12/2019 | Leyva et al. |
| 2020/0024167 A1 | 1/2020 | Leyva et al. |

FOREIGN PATENT DOCUMENTS

| | | |
|---|---|---|
| CN | 2905066 Y | 5/2007 |
| CN | 201156965 | 12/2008 |
| CN | 105031693 | 11/2015 |
| EP | 2731632 | 8/2017 |
| JP | 2005270589 | 10/2005 |
| KR | 1020040098412 | 11/2004 |
| WO | 03068274 | 8/2003 |
| WO | 2003068274 A2 | 8/2003 |
| WO | 2008116165 | 9/2008 |
| WO | 2011058472 | 5/2011 |
| WO | 2013012696 | 1/2013 |
| WO | 2015171730 | 11/2015 |

(56) References Cited

FOREIGN PATENT DOCUMENTS

| WO | 2017189915 | 11/2017 |
|----|------------|---------|
| WO | 2017189916 | 11/2017 |
| WO | 2018200525 | 11/2018 |

OTHER PUBLICATIONS

Office Action dated Jul. 29, 2019, issued in Chinese Patent Application No. 2017101790472, 8 pages.
Office Action dated August 6, 211019, issued in Chinese Patent Application No. 2017101795495, 9 pages.
Notice of Allowance dated Aug. 5, 2019, issued in U.S. Appl. No. 15/141,152, 8 pages.
Examination Report dated Aug. 13, 2019, issued in Australian Patent Application No. 2018200514, 6 pages.
Notice of Acceptance dated Aug. 14, 2019, issued in Australian Patent Application No. 2017228723, 4 pages.
Office Action dated Sep. 17, 2019, issued in U.S. Appl. No. 15/444,916, 17 pages.
Notice of Allowance dated Oct. 8, 2019, issued in Japanese Application No. 2017-149891, 4 pages.
Final Office Action dated Feb. 4, 2019, issued in U.S. Appl. No. 15/141,152, 14 pages.
Examination Report dated Feb. 15, 2019, issued in Australian Patent Application No. 2018200514, 5 pages.
Office Action dated Mar. 4, 2019, issued in U.S. Appl. No. 15/444,916, 16 pages.
Office Action dated Mar. 4, 2019, issued in U.S. Appl. No. 16/257,898, 13 pages.
Office Action dated Mar. 14, 2019, issued in U.S. Appl. No. 16/270,141, 12 pages.
Notice of Allowance dated Mar. 19, 2019, issued in U.S. Appl. No. 15/499,456, 12 pages.
U.S. Appl. No. 16/257,898, filed Jan. 25, 2019.
Office Action dated Apr. 2, 2019, issued in Japanese Patent Application No. 2017-0149891, 7 pages.
Notice of Allowance dated Apr. 30, 2019, issued in U.S. Appl. No. 15/441,929, 5 pages.
Office Action dated Feb. 3, 2020, issued in U.S. Appl. No. 16/190,996, 9 pages.
Office Action dated Feb. 18, 2020, issued in Canadian Patent Application No. 3,005,981, 3 pages.
Office Action dated Mar. 19, 2020, issued in Korean Patent Application No. 10-2020-7003298, 4 pages.
Office Action dated Mar. 23, 2020, issued in Chinese Patent Application No. 2017101790491, 8 pages.
Office Action dated Apr. 7, 2020, issued in U.S. Appl. No. 16/780,492, 13 pages.
Office Action dated Apr. 13, 2020, issued in U.S. Appl. No. 16/782,892, 15 pages.
Office Action dated Apr. 15, 2020, issued in U.S. Appl. No. 15/444,916, 16 pages.
Office Action dated Apr. 23, 2020, issued in U.S. Appl. No. 16/780,355, 14 pages.
Notice of Allowance dated Apr. 28, 2020, issued in U.S. Appl. No. 16/780,492, 7 pages.
ResMed VPAP III ST-A with QuickNav Clinical Guide, copyright 2008 ("ResMed Guide"). Cited by opposing counsel in connection with *SoClean Inc.* v. *Sunset Healthcare Solutions, Inc.*, Civil action No. 1:20-cv-10351-IT (U.S. Dist. Ct. Massachusetts).
VPAP IV and VPAP IV ST Product Training ("ResMed Presentation"). Cited by opposing counsel in connection with *SoClean Inc.* v. *Sunset Healthcare Solutions, Inc.*, Civil action No. 1:20-cv-10351-IT (U.S. Dist. Ct. Massachusetts). Publication Date is unknown to Applicant, but was asserted by opposing counsel in the noted litigation to be in 2008.
Examination Report dated Jun. 7, 2019, issued in Canadian Patent Application No. 3,005,981, 3 pages.

Preliminary Report on Patentability dated Nov. 7, 2019, issued in PCT Patent Application No. PCT/US2018/029140, 11 pages.
Notice of Allowance dated Nov. 15, 2019, issued in Australian Patent Application No. 2018200514, 4 pages.
Extended Search Report dated Nov. 29, 2019, issued in European Patent Application No. 17790471.1, 9 pages.
Examination Report dated Jan. 13, 2020, issued in Chilean Patent Application No. 201803063, 17 pages. English language machine translation included.
Ozone MSDS (Material Safety Data Sheets), Ozone Solutions, Jun. 1, 2000, http://www.ozoneapplications.com/info/ozone_msds.htm, 5 pages.
CPAP Guardian TB-316, America Tyson Industrial Group (Asia Pacific) Limited, http://www.ecvv.com/products/2314441.html, Nov. 91, 2009, downloaded from Internet Jul. 8, 2016, 3 pages.
International Search Report and Written Opinion dated Sep. 17, 2012, issued in PCT Application No. PCT/US12/46593, 6 pages.
International Search Report and Written Opinion dated Jul. 24, 2015, issued in PCT Application No. PCT/US15/29418, 9 pages.
U.S. Office Action dated Jun. 30, 2016, issued in U.S. Appl. No. 15/141,216, 13 pages.
U.S. Office Action dated Jul. 13, 2016, issued in U.S. Appl. No. 15/142,060, 18 pages.
U.S. Office Action dated Jul. 14, 2016, issued in U.S. Appl. No. 15/142,111, 10 pages.
U.S. Office Action dated Jul. 28, 2016, issued in U.S. Appl. No. 15/142,085, 15 pages.
U.S. Office Action dated Oct. 6, 2016, issued in U.S. Appl. No. 15/141,152, 11 pages.
U.S. Office Action dated Nov. 23, 2016, issued in U.S. Appl. No. 15/141,216, 9 pages.
U.S. Office Action dated Nov. 23, 2016, issued in U.S. Appl. No. 15/142,085, 8 pages.
U.S. Office Action dated Feb. 23, 2017, issued in U.S. Appl. No. 29/562,755, 8 pages.
U.S. Office Action dated Feb. 27, 2017, issued in U.S. Appl. No. 29/562,756, 7 pages.
U.S. Office Action dated Mar. 17, 2017, issued in U.S. Appl. No. 15/141,152, 14 pages.
U.S. Office Action dated Jun. 13, 2017, issued in U.S. Appl. No. 15/481,919, 10 pages.
International Search Report and Written Opinion dated Aug. 2, 2017, issued in PCT Patent Application No. PCT/US17/29949, 11 pages.
U.S. Office Action dated Aug. 3, 2017, issued in U.S. Appl. No. 15/141,152, 14 pages.
International Search Report and Written Opinion dated Aug. 16, 2017, issued in PCT Patent Application No. PCT/US17/29950, 11 pages.
Office Action dated Sep. 21, 2017, issued in U.S. Appl. No. 15/142,085, 9 pages.
Notice of Allowance dated Oct. 13, 2017, issued in U.S. Appl. No. 15/481,919, 7 pages.
U.S. Final Office Action dated Feb. 5, 2018, issued in U.S. Appl. No. 15/141,152, 16 pages.
U.S. Office Action dated Apr. 3, 2018, issued in U.S. Appl. No. 15/873,506, 7 pages.
U.S. Notice of Allowance dated Apr. 27, 2018, issued in U.S. Appl. No. 15/142,085, 8 pages.
International Search Report and Written Opinion dated Jul. 13, 2018, issued in PCT International Patent Application No. PCT/US18/29140, 12 pages.
Office Action dated Aug. 9, 2018, issued in Japanese Patent Application No. 2014-520352, 5 pages. English language translation provided.
Office Action dated Sep. 5, 2018, issued in Chinese Patent Application No. 2016105175158, 10 pages. English anguage translation provided.
Office Action dated Sep. 17, 2018, issued in U.S. Appl. No. 15/441,929, 10 pages.
Examination Report dated Sep. 26, 2018, issued in Australian Patent Application No. 2017228723, 6 pages.

(56) References Cited

OTHER PUBLICATIONS

Office Action dated Oct. 30, 2018, issued in U.S. Appl. No. 15/499,456, 13 pages.
Notice of Allowance dated Oct. 31, 2018, issued in U.S. Appl. No. 15/873,506, 8 pages.
Office Action amendment dated Oct. 31, 2018, issued in U.S. Appl. No. 15/499,456, 13 pages.
Office Action dated Nov. 6, 2018, issued in U.S. Appl. No. 15/499,378, 18 pages.
Preliminary Report on Patentability dated Nov. 8, 2018, issued in PCT International Patent Application No. PCT/US2017/029949, 9 pages.
Preliminary Report on Patentability dated Nov. 8, 2018, issued in PCT International Patent Application No. PCT/US2017/029950, 9 pages.
Office Action dated Jan. 16, 2019, issued in Korean Patent Application No. 10-2018-7009274, 5 pages. English language translation provided.
Notice of Allowance dated Jan. 18, 2019, issued in U.S. Appl. No. 15/441,929, 7 pages.
Office Action dated Jan. 22, 2019, issued in U.S. Appl. No. 16/190,996, 10 pages.
Examination Report dated May 15, 2019, issued in Australian Patent Application No. 2017228723, 5 pages.
Notice of Allowance dated May 17, 2019, issued in U.S. Appl. No. 16/270,141, 7 pages.
Notice of Allowability dated May 22, 2019, issued in U.S. Appl. No. 15/499,456, 5 pages.
Notice of Allowance dated May 28, 2019, issued in U.S. Appl. No. 15/499,378, 7 pages.
Notice of Allowance dated Jun. 20, 2019, issued in U.S. Appl. No. 16/257,898, 8 pages.
U.S. Office Action dated Jul. 26, 2019, issued in U.S. Appl. No. 16/190,996, 12 pages.
Lenntech "Ozone Generation", Wayback Machine Capture, Mar. 28, 2010, (Year 2010), 3 pages.
Office Action from related Japanese Appln. No. 2018-554099, dated Feb. 1, 2021. English translation attached. 11 pages.
Office Action from corresponding U.S. Appl. No. 15/880,962, dated Jan. 15, 2021. 21 pages.
Second Office Action from related Chinese Appln. No. 201701786388, dated Jul. 3, 2020. English translation attached. 15 pages.
First Office Action from related Chinese Appln. No. 2017101786388, dated Aug. 23, 2019. English translation attached. 15 pages.
Third Office Action from related Chinese Appln. No. 2017101786388, dated Jan. 8, 2021. English translation attached. 13 pages.
Office Action from related Russian Appln. No. 2018136948, dated Oct. 13, 2020. English translation attached. 19 pages.
Office Action from related Russian Appln. No. 2018136948, dated Apr. 27, 2021. English translation attached. 17 pages.
Office Action from related Russian Appln. No. 2018136948, dated Sep. 15, 2021. English translation attached. 21 pages.
Office Action from related Indian Appln. No. 201827043772 dated May 10, 2021. English translation attached. 8 pages.

\* cited by examiner

DEVICES, SYSTEMS AND METHODS FOR TREATING MULTIPLE MEDICAL DEVICES HAVING PASSAGEWAYS WITH OZONE GAS

CROSS REFERENCE TO RELATED APPLICATION

This application is a continuation of U.S. patent application Ser. No. 15/141,152, filed Apr. 28, 2016, which is a continuation in part of PCT International Patent Application Serial No. PCT/US2015/029418, filed May 6, 2015. Said U.S. patent application Ser. No. 15/141,152, filed Apr. 28, 2016, is also a continuation in part of U.S. patent application Ser. No. 14/232,773 (now U.S. Pat. No. 9,358,316) filed Jan. 14, 2014, which is a 371 of International Patent Application Serial No. PCT/US2012/046593, filed Jul. 13, 2012, which claims the benefit of U.S. Provisional Patent Application Ser. No. 61/508,341, filed Jul. 15, 2011, the entire disclosures of all of the above listed application are incorporated herein by reference.

TECHNICAL FIELD

The present disclosure generally relates to devices, systems and methods using agents or gas, such as ozone gas, for cleaning, disinfecting and sanitizing multiple medical devices for reuse and reprocessing. In particular the present disclosure relates to devices, systems and methods to clean, disinfect and/or sterilize inner compartments, hoses and tubes and enclosed spaces on multiple medical devices, as further disclosed herein.

BACKGROUND

All devices, instruments and accessories used for medical purposes (collectively "medical devices") require varying degrees of cleaning, disinfection and sterilization before the devices can be reprocessed and reused on the same patient, or between patients. In particular, devices with passageways, such as hoses and tubes, are particularly difficult to reuse as the inner space of the passageway, is difficult to completely clean, disinfect and sterilize. These hard to reach places are particularly prone to bacteria, mold and microorganism build-up as medical devices often have fluid, other devices touching fluids or body parts, water and humidified water passing through the passageways. As such, there is a need for devices, systems and methods that solves the need to clean, disinfect and sterilize multiple medical devices, including the inner passageways of medical tubes.

Institutions such as hospitals, surgical centers, medical test centers, sleep centers, nursing homes and the like often have the need to reuse medical devices between patients. In hospitals, for example, a variety of devices may require a specific level of cleaning, disinfection, sterilization or a combination thereof before those devices can be reused on the same patient or between patients. Non-compliance with required cleaning, disinfecting, and sterilizing schedules by institutions may result in serious risk to a patient. Currently, institutions have no ability to clean, disinfect, and/or sterilize multiple medical devices, to assure that all of the device parts are ready to be reused in accordance with the devices risk of microbial, microorganism infection and soil build-up. Institutions thus often dispose of medical devices, and use new devices on each patient or between uses on the same patient, resulting in a significant expense. Alternatively, institutions often hire employees to wash devices, in specialized solvents, also resulting in a significant expense for the institution along with a possible margin of error.

Medical devices can be classified in terms of potential risk of infection towards a patient or between patients if the medical device is reused. As an example medical devices may be classified as critical, semi-critical, and non-critical to describe their risk of infection if the devices are reused on the same patient and/or reused between patients. Example of critical devices include but are not limited to, surgical instruments, irrigation systems for sterile instruments in sterile tissues, endoscopes and endoscopic biopsy accessories. These critical devices, for instance, are devices that are introduced directly in the bloodstream or may contact normally sterile tissue and have a possibility of microbial transmission if the medical device is not sterile, thus strict cleaning and sterilization of the medical device is required. Semi-critical devices may be categorized as devices that contact mucous membranes, for example, duodenoscopes, endotracheal tubes, bronchosopes, laryngosopes, blades and other respiratory equipment, esophageal manometry probes, diaphragm fitting rings and gastrointestinal endoscopes, which may require disinfection and/or sterilization before a device can be reused. Non-critical devices are medical devices whose surfaces contacts the skin but do not penetrate the skin. Non-critical devices also include devices that may become contaminated with microorganisms and organic soil during patient care, such as infusion pumps, and ventilators, for example continuous positive airway pressure devices, prone to bacterial build-up because of humidified air and contact with a patient's mouth. Many of the devices listed above include passageways that are difficult to clean, disinfect and sterilize, such as endoscopes, probes, ventilators and specifically continuous positive airway pressure devices and related hoses.

It is thus an object of the present disclosure to provide devices, systems and methods for institutions to clean, disinfect and/or sterilize multiple medical devices. It is also a long-felt need in the art to provide devices, systems and methods that can clean, disinfect and sterilize the inner passageways, tubes and hoses of multiple medical devices while also cleaning, disinfecting and/or sterilizing the outer areas of the medical devices. It is further a long-felt need in the art to indicate to a user at the institution when medical devices are safe to be reused after a treatment cycle. There is also a need to indicate to a user cycle feedback throughout a cleaning, disinfecting and/or sterilizing cycle, to indicate to the user that the device has reached for instance, the maximum level of gas output required to fully sterilize a medical device, allowing the user to know that the devices have been fully sterilized and that there has been no error in reaching the necessary gas sterilization levels and completing a sterilization cycle. There is further a need to provide a device, systems and methods that can attach to any medical device passageway to treat the passageway with ozone gas.

Other systems, methods, apparatus features, and advantages of the present disclosure will be or become apparent to one with skill in the art upon examination of the following drawings and detailed description. It is intended that all such additional systems, methods, apparatus features, and advantages be included within this description, be within the scope of the present disclosure, and be protected by the accompanying claims.

BRIEF DESCRIPTION OF THE DRAWINGS

Many aspects of the disclosure can be better understood with reference to the following drawings. The components in the drawings are not necessarily to scale, emphasis instead being placed upon clearly illustrating the principles of the present disclosure. Moreover, in the drawings, like reference numerals designate corresponding parts throughout the several views.

SUMMARY OF THE DISCLOSURE

The present disclosure relates to devices, systems and methods for cleaning, disinfecting and sterilizing multiple medical devices, wherein each of the medical devices includes a passageway, the device comprising: a housing including a base, side walls extending from the base, and a cover forming a gas-tight compartment when the cover is in a closed position over the side walls, wherein the gas-tight compartment is sized and configured to receive the multiple medical devices; at least two ozone ports fluidly coupled with the gas-tight compartment, each of the ozone ports being configured to engage at a distal end with a proximal end of a passageway such as a tube or a hose of one of the devices; and, an ozone operating system connected with a distribution line at a proximal end of the at least two ozone ports for delivering ozone through the ozone ports.

DETAILED DESCRIPTION

Figure 1:
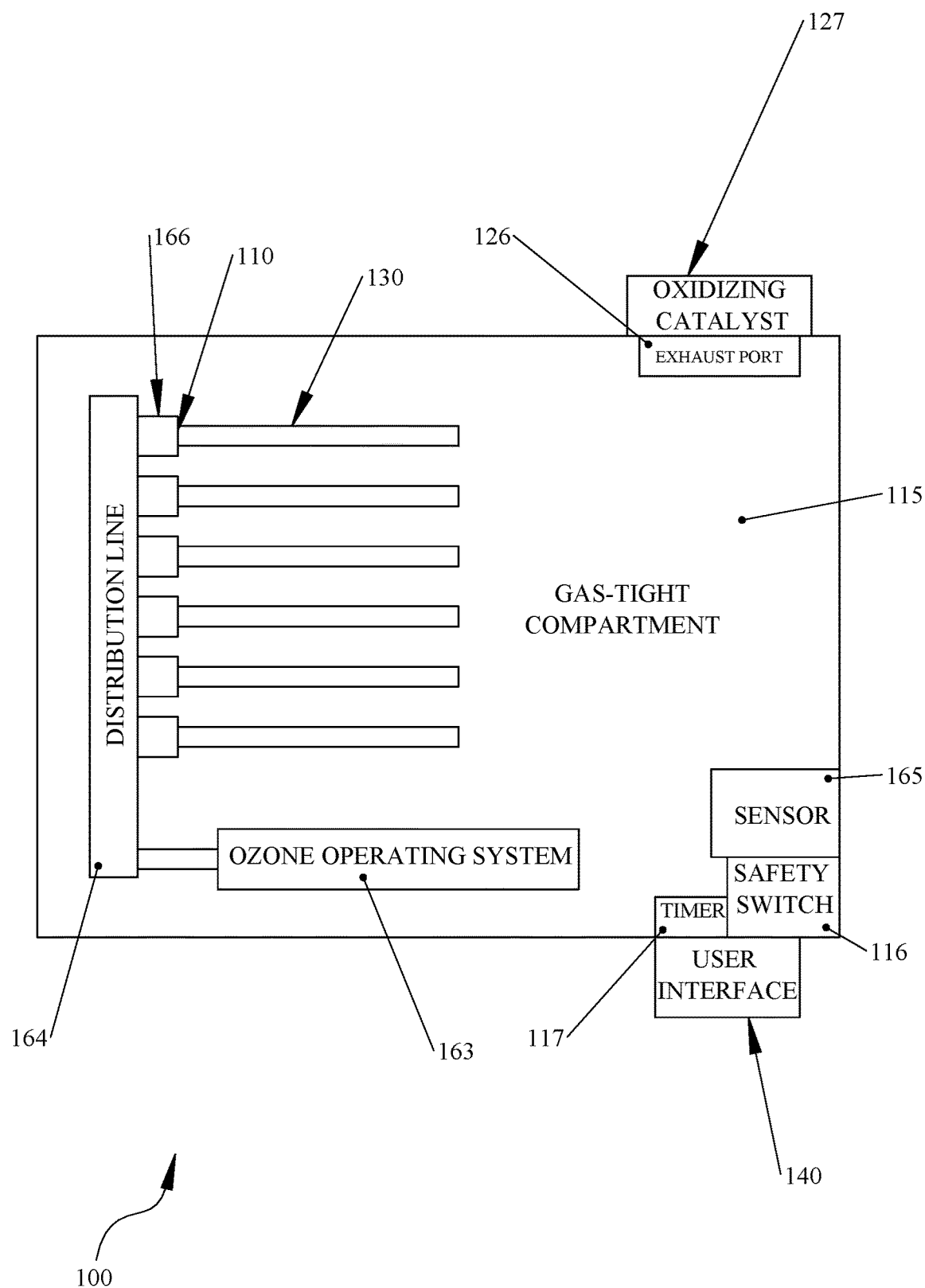
FIG. 1 is a schematic diagram of a multi-channel ozone treatment system for treating a plurality of medical devices with ozone in accordance with one embodiment of the present disclosure.

FIG. 1 is a schematic diagram showing, a multi-channel ozone treatment device and system including an ozone operating system, a multi-channel ozone distribution system, a compartment and an exhaust system, for cleaning, disinfecting and/or sterilizing multiple medical devices. Multiple ozone ports connected to the multi-channel ozone distribution system. The multi-channel ozone treatment system includes a user interface, a sensor for detecting operations of the systems, a timer and a safety switch. Further, as shown, an oxidizing catalyst may be included in the exhaust system.

In accordance with the embodiment shown in FIG. 1 the flow of ozone gas in one embodiment of the multi-channel ozone treatment device 100 is shown in accordance with the present disclosure. In accordance with this embodiment, an ozone operating system 163 is embedded in a device 100. In this embodiment a distribution line 164 is provided to carry ozone gas from the ozone operating system to distribute the ozone to multiple ozone ports 110 in the multi-channel ozone treatment device 100. The distribution line 164 splits into a plurality of distribution channels 166 that each connect to the proximal end of an ozone port 110, such that each ozone port 110 is connected to a channel 166 of the distribution line 164 at the proximal end of the ozone port and the ozone port 110 connects fluidly to a passageway 130 of multiple medical devices either alone through the port itself, or with an adapter such as a connector unit, as described in the further embodiments herein. The medical devices may include any medical devices with passageways including, without limitation, tubes and hoses. As shown in the sketch of FIG. 1, a gas-tight compartment 115 is provided for housing and treating a medical device and the inner passageway of medical device tubes 130 in accordance with the present disclosure. As used herein, treating with ozone refers to the use of ozone gas to clean, disinfect, sanitize and/or sterilize. Thus in accordance with this embodiment and the sketch shown, ozone gas will enter the distribution line 164 and each channel 166 connected to the ozone ports 110, the ozone will traverse into the ozone ports 110 and the connected medical tubes 130, thereby cleaning, disinfecting and sterilizing multiple medical passageways 130. An air pump as part of the ozone operating system in this embodiment pushes the ozone gas in the desired direction, through the distribution line 164 and channels 166, into the ozone ports 110, and into the medical tubes 130. Ozone will then release into the gas-tight compartment 115 and treat medical devices placed in the gas-tight compartment 115. In addition a UVC light may be used to further clean, disinfect and sterilize medical devices in the gas-tight compartment 115. An exhaust port 126 with an oxidizing catalyst 127 may be used to provide for slow and safe removal of ozone and release of oxygen (converted from ozone) from the multi-channel ozone treatment device 100 into the ambient environment.

As shown in FIG. 1, the multi-channel ozone treatment device 100 may include a sensing system for detecting levels of ozone gas in the gas-tight compartment 115, a safety switch 116, a timer, 117 and a user interface 140 for displaying cycle information and for setting cleaning, disinfecting and sterilizing cycle. The sensors 165 in accordance with the present embodiment allow a user to know if a medical device is ready for reuse, as an indicator and test that the devices, systems and methods in accordance with the present embodiment reached the required ozone level to treat medical devices encased in the gas-tight compartment 115. If, for example, the required ozone level is 50 for sterilizing a laryngoscope, and the maximum ozone level reached in a cycle is 40, a user will know that the sterilization cycle is incomplete, and that the encased laryngoscopes are not ready for reuse on the same patient or to be used from patient to patient. If the sensor indicates that the maximum ozone level of 50 has been obtained, the user will know that the laryngoscope is ready for reuse. The sensors 165 may be located anywhere on the multi-channel ozone treatment device, and may comprise of one or more sensors 165 on the multi-channel ozone treatment device 100 and the sensors 165 may be couple to the exhaust port 126. Other indicators such as light displays, sound indicators, led light signals, and color indicators including but not limited to a color coded smoke, color coded lines and a color coded windows, may be used to indicate to a user whether or not the encased medical devices being treated are ready for reuse. The indicators may be tied to the sensors for detecting ozone gas levels in the gas-tight sterilization compartment 115.

Figure 2:
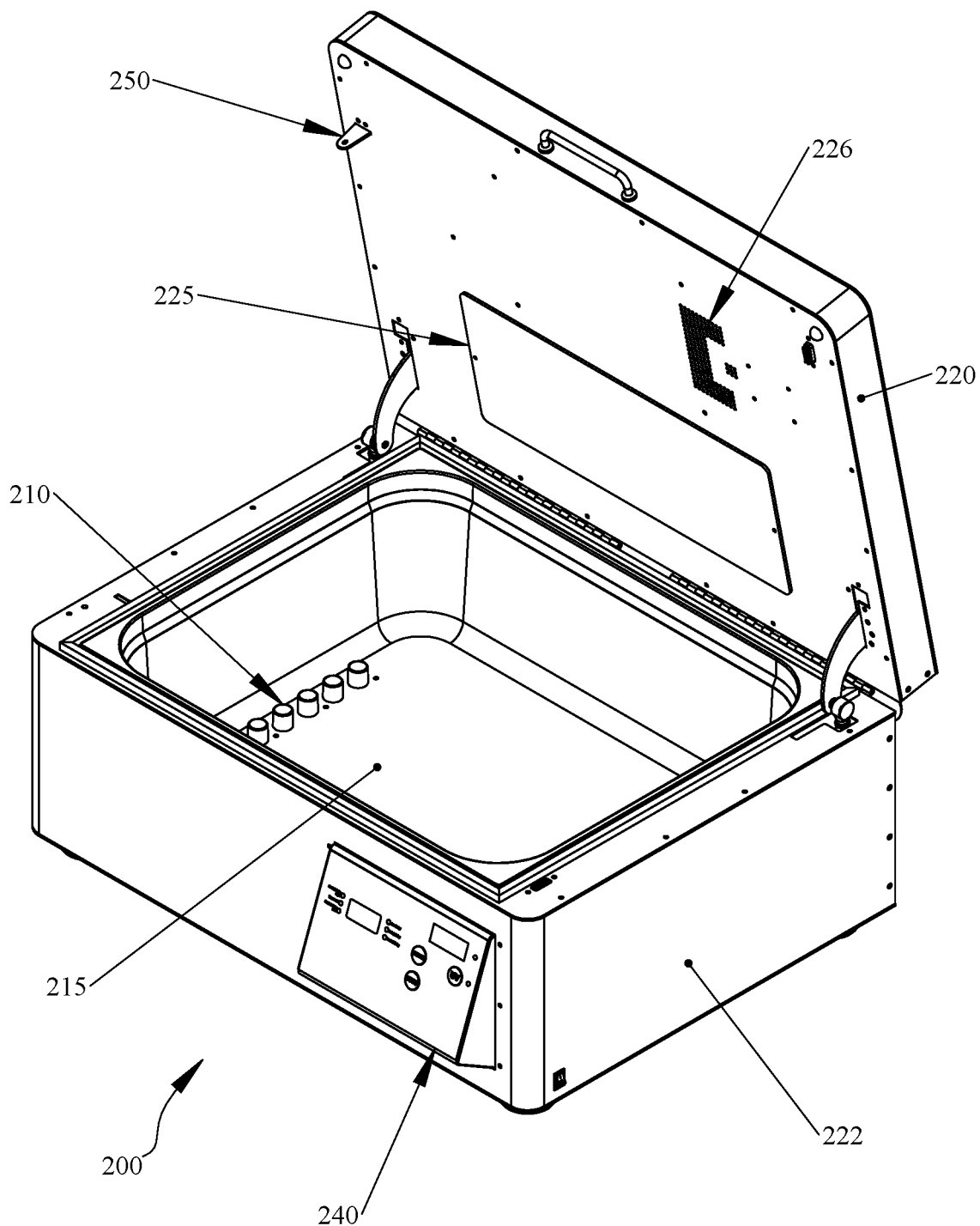
FIG. 2 is a perspective view of an ozone treatment device for treating multiple medical devices with ozone, consistent with an embodiment of the present disclosure.

FIGS. 2-5 show one embodiment of a multi-channel ozone treatment device 200. FIG. 2 is a perspective view of the multi-channel ozone treatment device 200 for cleaning, disinfecting, and/or sterilizing medical devices and medical device passageways in accordance with one embodiment of the present disclosure. In accordance with this embodiment, an ozone operating system is located behind a compartment door on the bottom side of the multi-channel ozone treatment system 200. In this embodiment, a distribution line and distribution channels carry ozone from the ozone operating system to each ozone port 210 in the multi-channel ozone treatment system 200. In accordance with this embodiment, the gas-tight compartment 215 is provided for cleaning, disinfecting and/or sterilizing the medical device and the passageway of a medical device when the cover 220 is in a closed position. The gas-tight compartment 215 is thus sized and configured to accept multiple medical devices. In addition, on the cover 220, is a UV light compartment 225, with a UV light to further clean, disinfect and sterilize bacteria on the medical device and medical tubes encased in the gas-tight compartment 215. UVC light essentially works by destroying nucleic acids and disrupting the DNA of microorganisms on device parts in accordance with the embodiments of the present disclosure. Having the UVC light directly above the medical devices and medical device tubes in the gas-tight compartment 215 during a cycle further treats the encased parts by using short-wavelength ultraviolet light to kill or inactivate microorganisms. In accordance with this embodiment, the UV light may be a UVC type light emitting UV light of about a 254 nm wavelength, in other embodiments the wavelength may be about 100 nm to about 280 nm.

In addition, in accordance with the present embodiment, a user interface 240 is provided for initiating a cycle, displaying cycle time and sensory input and output, and indicating completion of a cycle to a user. A locking mechanism 250 is further used in accordance with the present embodiment to securely lock the cover 220 to the sidewalls 222 of the multi-channel ozone treatment system 200 when the device 200 is in an on position, in accordance with this embodiment. The locking mechanism 250 ensures safe use of the device 200 to manage and control release of high levels of ozone gas used in the present embodiment to treat multiple medical devices and medical passageways such as tubes and hoses, providing for a the multi-channel ozone treatment system 200 with controlled ozone release systems and methods. In this embodiment, an exhaust port 226 is further provided for controlled release of ozone in the ambient environment when the ozone $O^3$ has converted back to oxygen $O^2$. In accordance with this embodiment, a magnesium oxide ($MGO^2$) filter is coupled to the exhaust port 226 on the cover 220 to provide for slow release of ozone from the gas-tight compartment 215 when a cleaning, disinfecting, and/or sterilizing cycle has completed, for safe decomposition of ozone into the ambient environment in accordance with the present embodiment.

Figure 3:
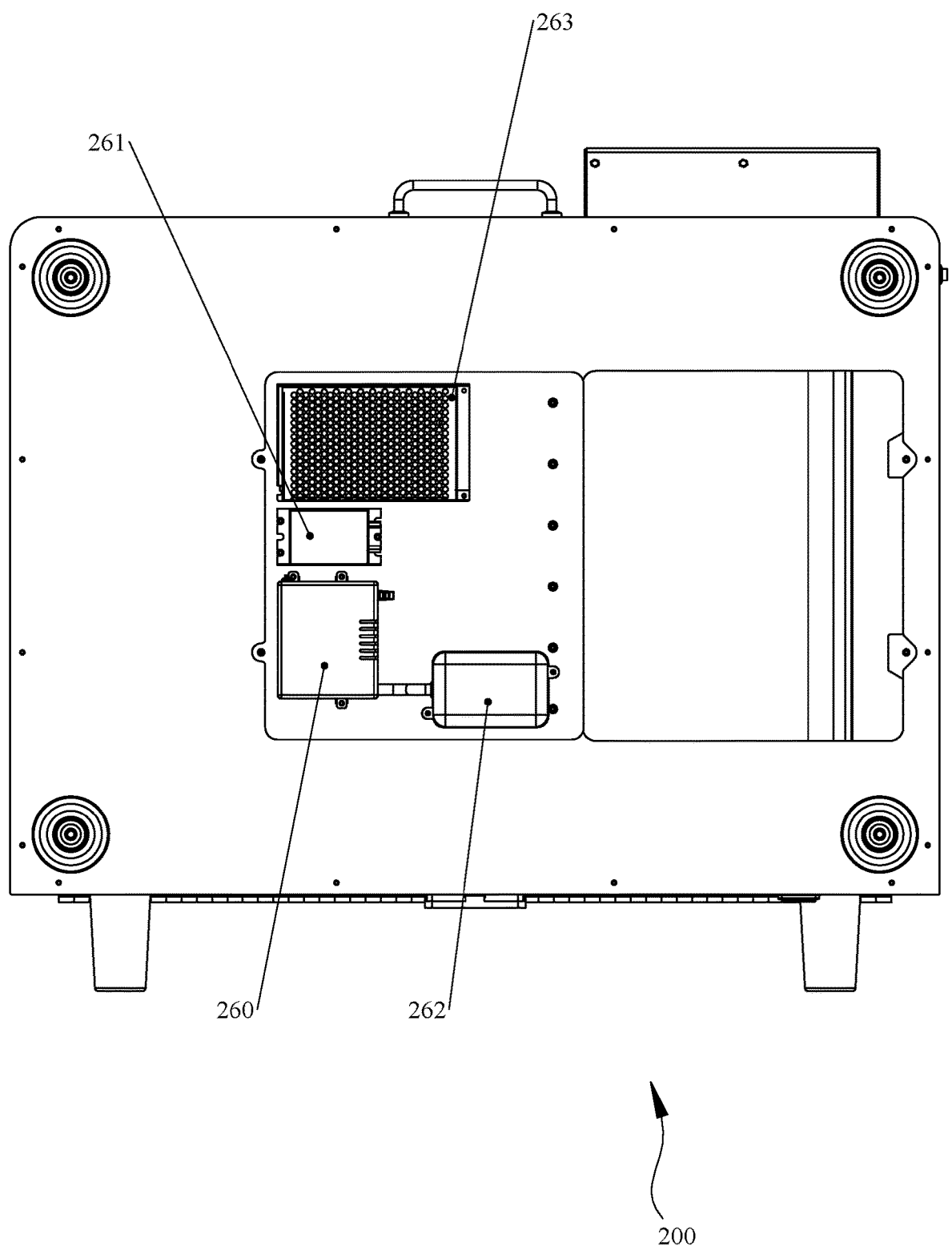
FIG. 3 is a bottom view of the ozone treatment device shown in FIG. 2.

FIG. 3 is a bottom view of the multi-channel ozone treatment device 200 in accordance with an embodiment of the present disclosure. In accordance with this embodiment an ozone generator 260 is shown attached to an air pump 262. Further shown in the bottom view is an AC to DC voltage converter 263 attached to a UVC balast component 261, for managing power to the UVC light in accordance with the present embodiment of the disclosure. In accordance with this embodiment a UVC bulb is provided in the cover of the device 200, the UVC bulb in this embodiment provides light with a wavelength of 254 nm directed into the gas-tight compartment 215 to the component parts of the medical devices when the cover is in a closed position and a cycle is in an on position. In other embodiments the UVC power may also be 100 nm to 280 nm.

Figure 4:
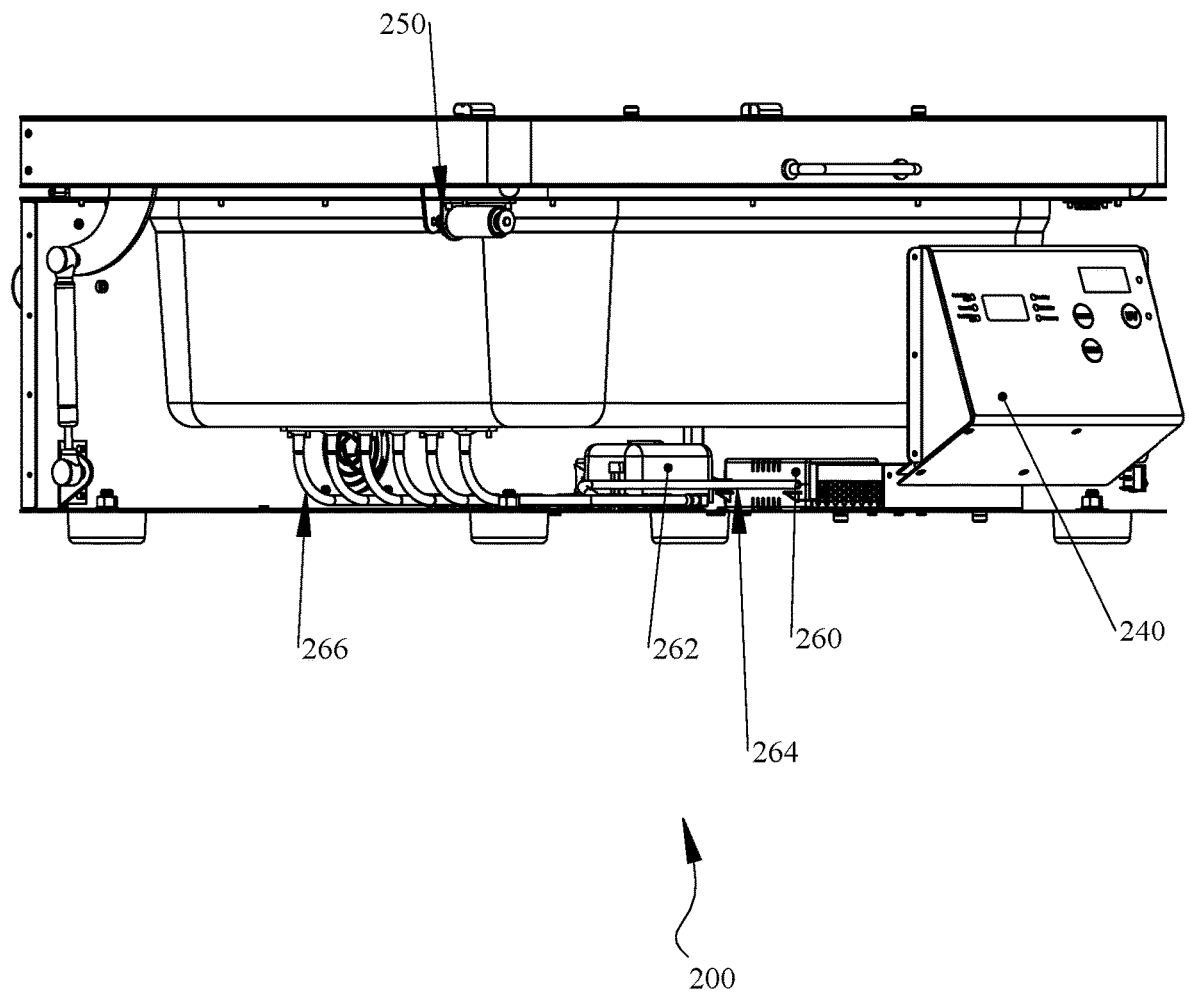
FIG. 4 is a side perspective view of the ozone treatment device shown in FIG. 2 with the side-wall removed.

FIG. 4 shows a perspective view of the multi-channel ozone treatment device 200 in accordance with an embodiment of the present disclosure. In accordance with this embodiment, a plurality of distribution channels 266 are extending from the distribution line 264. In accordance with this embodiment the ozone generator 260, such as an ozonator, generates ozone and distributes the ozone through distribution line 264 into the plurality of distribution channels 266 and into the ozone ports. Ozonators create ozone from oxygen molecules, often by applying ultraviolet light or corona discharge to oxygen. Ozone gas is made of three oxygen molecules that have been ionized by radiation to form groups of three oxygen atoms, $O^3$. Ozone gas is powerful and effective for removal of odors, impurities and dangerous pathogens, working by exchanging electron charge with particles that ozone comes into contact to form oxygen $O^2$ from the unstable ozone $O^3$. In accordance with this embodiment an air pump 262 is shown connected to the ozone generator 260 on the side opposite of the distribution line 264, the air pump 262 pushes ozone from the ozone generator 260 into the distribution line 264. The air pump 262 combined with the ozone generator 260 in accordance with this embodiment creates about 100-1000 mg/hr of ozone gas. An aquarium pump, for example, may be used as the air pump 262 in accordance with the present embodiment. The present embodiment further shows the user interface 240 for starting, stopping and displaying cleaning, disinfecting and sterilization information to a user, and a locking mechanism 250 for securely closing the multi-channel ozone treatment device 200 by a user.

Figure 5:
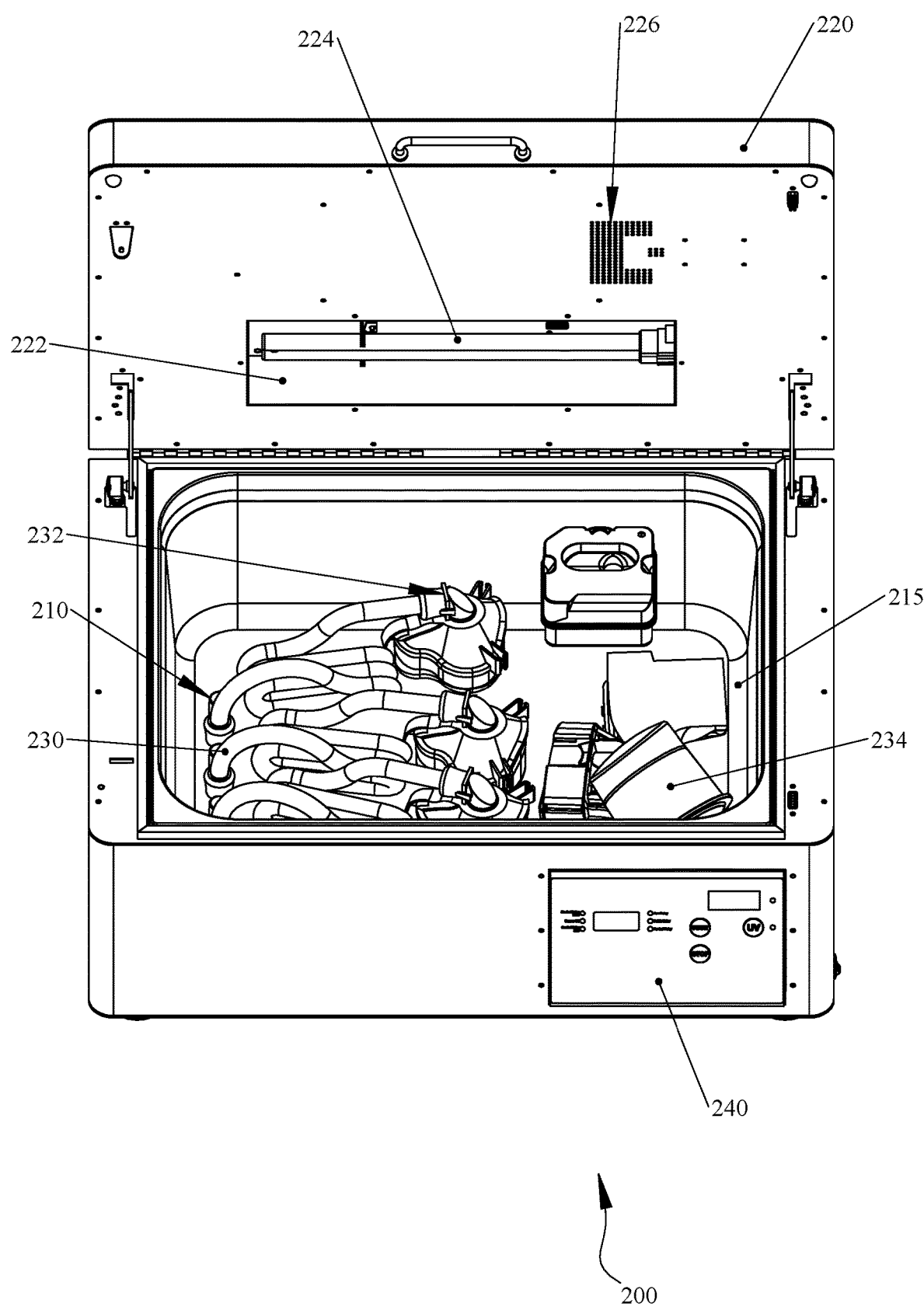
FIG. 5 is a top perspective view of the device shown in FIG. 2.

FIG. 5 shows a top view of a multi-channel ozone treatment device 200 with the cover 220 in an open position. While the multi-channel ozone treatment device 200 is effective for multiple types of medical devices and medical device tubes and passageways, by way of example the present embodiment is shown with multiple continuous positive airway pressure (CPAP) devices placed in the gas-tight compartment 215. In accordance with this embodiment, the hoses 230, facemasks 232, and water reservoirs 234 of multiple CPAP devices are shown in the gas-tight compartment 215. In this embodiment ozone ports 210 are attached at the distal end to the proximal end of the hoses 230. As described in FIG. 2, ozone is released into the ozone ports 210 from a plurality of distribution channels attached to a distribution line and an ozone generator, so that ozone migrates from the ozone ports 210, through the inside of the hoses 230, and the facemasks 232, thereby cleaning, disinfecting, and sterilizing the inner cavities of the hoses 230 and the facemasks 232. The ozone is then released from the facemask into the gas-tight compartment 215, and continues to clean, disinfect and sterilize the outer walls of the hoses 230 and the facemasks 232, along with the water reservoir 234 of the CPAP device. Cover 220 further contains a UVC light compartment 225 with a UVC light 224. In accordance with this embodiment when the cover 220 is in a closed and sealed position for a treatment cycle, the UVC light will further sanitize, clean, disinfect and sterilize the hoses 230, the facemasks 232, the water reservoirs 234, along with any other devices, medical instruments, supplies or the like, placed in the gas-tight compartment 215. In this embodiment, three CPAP devices are shown being cleaned, disinfected and sterilized in one cycle, however in other embodiments about two to one-hundred CPAP devices can be cleaned, disinfected and/or sterilized with the device 200 disclosed herein.

In addition in another embodiment of the present disclosure a method of treating by cleaning, disinfecting and/or sterilizing multiple continuous positive airway pressure devices wherein each of the continuous positive airway pressure devices includes a hose and a mask connected to the hose is described, the method, comprising the steps of: attaching the hose of each of the devices to a respective ozone port in a compartment and enclosing the devices in the compartment such that the compartment is air-tight; producing ozone with an ozone operating system; releasing ozone from the ozone operating system into the ozone ports; and migrating the ozone through, the hose, the mask and the gas-tight compartment. The method in accordance with this embodiment further includes the step of providing an ultraviolet light directed into the gas-tight compartment. The present embodiment further includes the step of releasing ozone from the gas-tight compartment through an exhaust port and the step of providing a sensor for detecting release of ozone from the gas-tight compartment. In accordance with this method a magnesium oxide (MGO$^2$) filter may be coupled to the exhaust port for releasing ozone slowly into the ambient environment. In accordance with this embodiment the gas-tight compartment is also sized and configured to receive additional medical device parts, such as, for example, water reservoirs of two or more continuous positive airway pressure devices.

In less than one minute from the start of the ozone process described, the ozone will start to naturally breakdown into oxygen $O_2$, which can then be safely released into the ambient environment or recycled. Sensors in the ozone system detect ozone levels during and after a cycle to make sure a cycle has reached the maximum required ozone levels for proper cleaning, disinfection and sterilization, and to allow a user to know when a device is safe to open and remove medical devices. As an additional safety precaution to make sure all ozone is released, an exhaust port is provided coupled to the cover, and coupled to an oxidizing catalyst, such as an $MGO_2$ filter, to collect, breakdown and release remaining ozone as oxygen $O_2$. Further in accordance with this embodiment, a built-in timer and start button allows a user to simply press a start button and an ozone cycle in accordance with this embodiment of the present disclosure is initiated. The timer in this embodiment controls release of ozone into the gas-tight compartment. Sensors display ozone levels to a user on the user interface, for example, if the required ozone level is indicated by the number 50 on the user interface, and the indication is only 40, then a user knows that the treatment cycle is incomplete, and the medical devices and equipment being cleaned are not ready for reuse. FIG. 5 further shows a user interface 240 in accordance with the present embodiment, providing start/stop control buttons, cycle information, and cycle signals and displays for initiating, reviewing and completing a treatment cycle.

Figure 6:
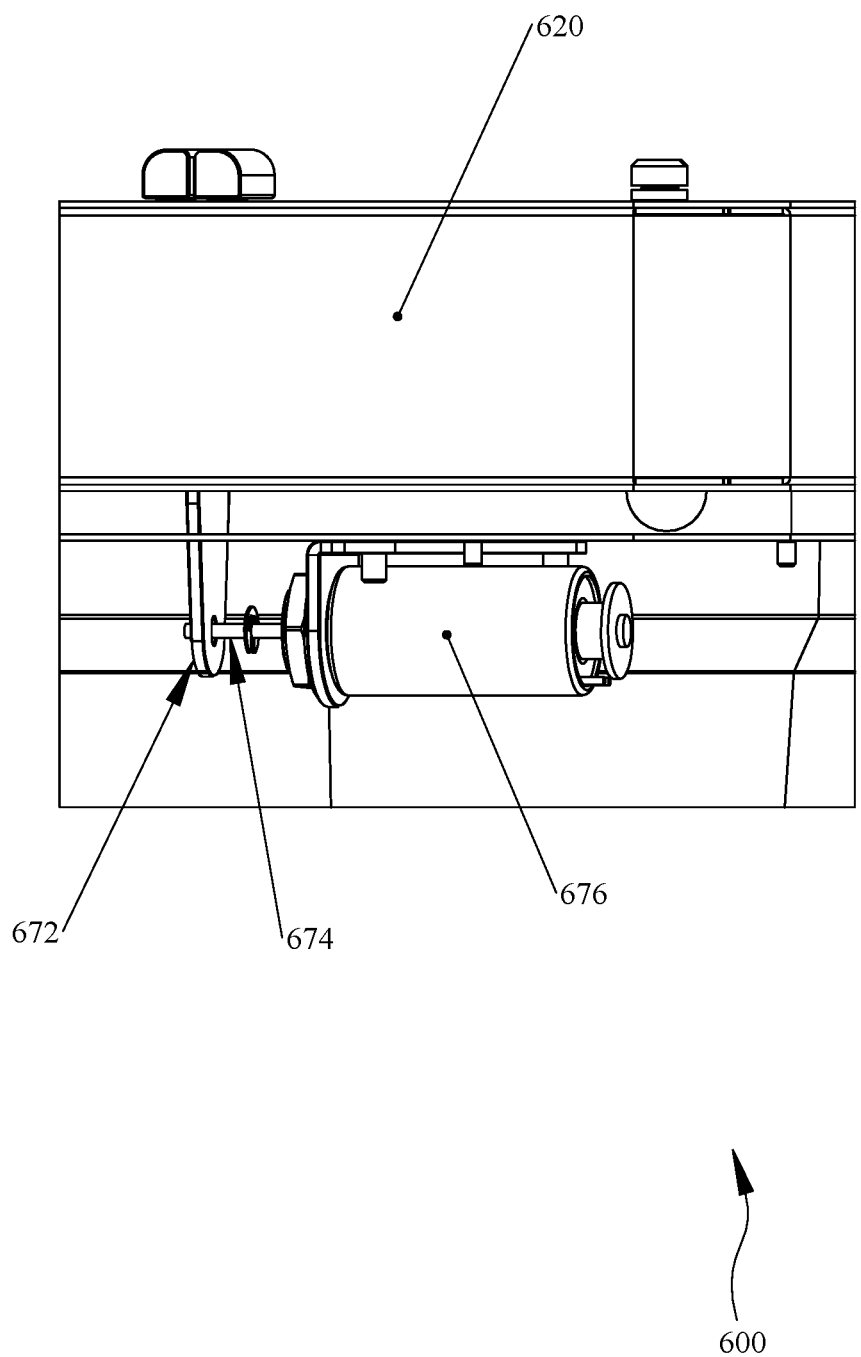
FIG. 6 is a side perspective view of a locking mechanism to securely close a multi-channel ozone treatment device, consistent with embodiments of the present disclosure.

FIG. 6 shows an embodiment of a locking mechanism 600 embedded in the cover 620 in accordance with an embodiment of the present disclosure. In accordance with this embodiment a bracket 672 with a hole is provided for closing the cover 620 over the gas-tight compartment. In accordance with this embodiment a solenoid pin 674 will traverse from a solenoid lock 676 into the hole in the bracket 672 when the cover 620 is in a closed position. An indicator on the user interface is provided when the solenoid pin 674 is in a closed position and securely locked, to maintain safe use of a multi-channel ozone treatment device for multiple CPAP devices.

Figure 7A:
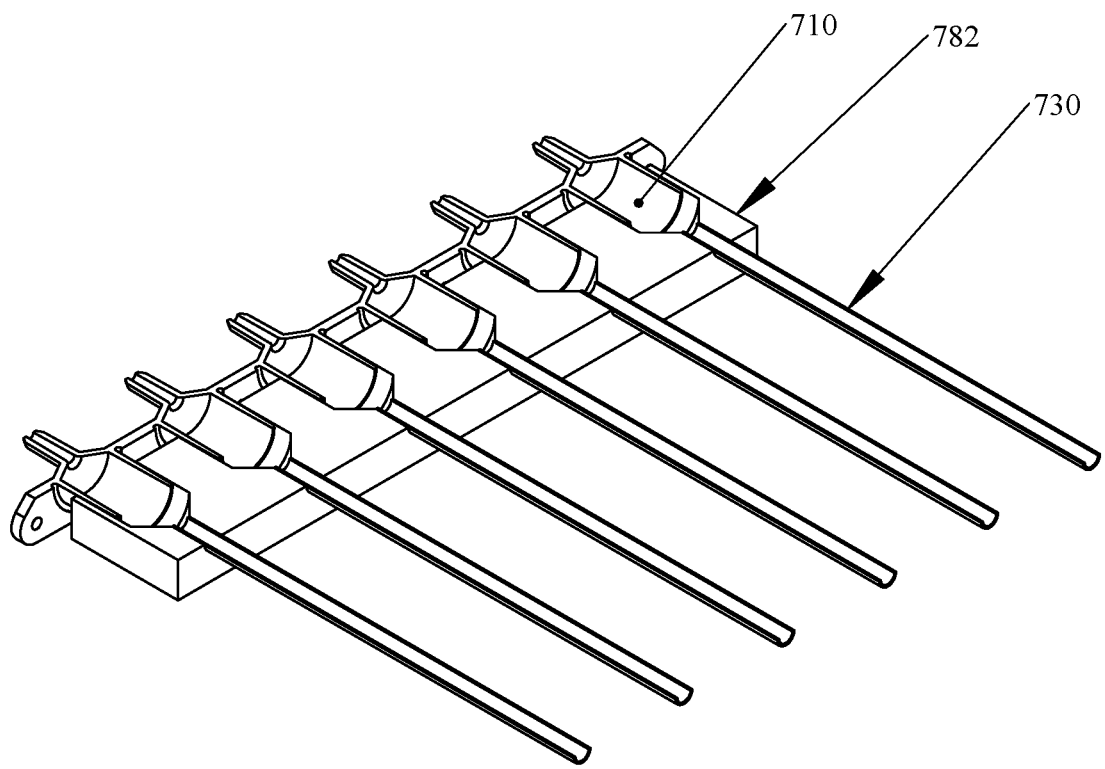
FIG. 7A is a cross-section view of a multi-channel connector unit for securely connecting medical device tubes to a plurality of ozone ports, consistent with an embodiment of the present disclosure.
Figure 7B:
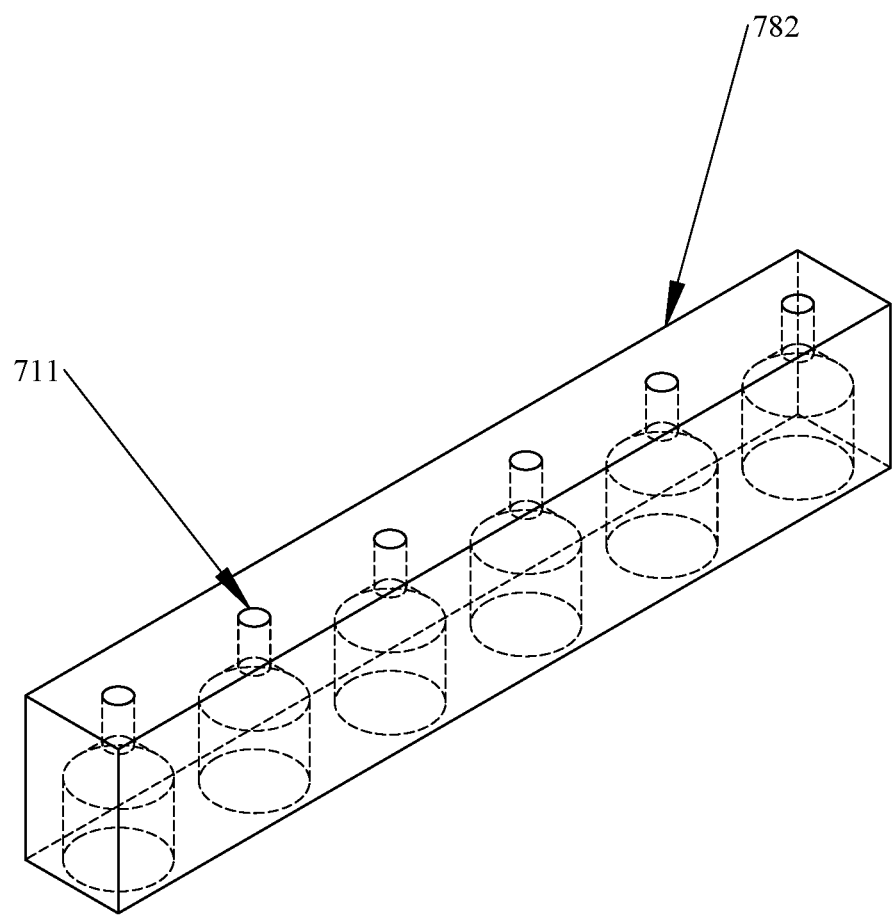
FIG. 7B is a perspective view of the multi-channel connector unit shown in FIG. 7A.

FIGS. 7A and 7B show a multi-port connector unit 782 connected to the ozone port 710 to alter the size of the ozone port 710 to fluidly couple to a tube 730 of any medical device. In accordance with this embodiment, the multi-port connector unit 782 is shown fluidly coupling an endoscope having a small proximal opening 711 to an ozone port 710 with a significantly larger distal opening, such that a user can interchangeably use the multi-channel ozone treatment device disclosed in the above embodiments to a variety of different medical devices with medical tubes, in order to clean, disinfect and sterilize the inner space of the medical device tube. The connector unit 782 can be sized to adapt the ozone ports to fluidly connect to any medical device tube. In accordance with the embodiment shown, the ozone ports 710 shown fit securely around the hose of a CPAP device, however with the multi-port connector unit 782 secured to the ozone ports 710 in a gas-tight sterilization compartment, endoscopic tubes 730 can be attached to the ozone ports and readily treated using one device that can clean, disinfect and sterilize multiple different products, in accordance with an embodiment of the present disclosure. As is apparent from the present disclosure, an adapter for any medical device with a tube can be used to connect the medical device tube 730 to the ozone ports 710 of the present embodiment, thereby providing users with a wide array of devices that can be cleaned, disinfected and/or sterilized in the present embodiment.

Figure 7C:
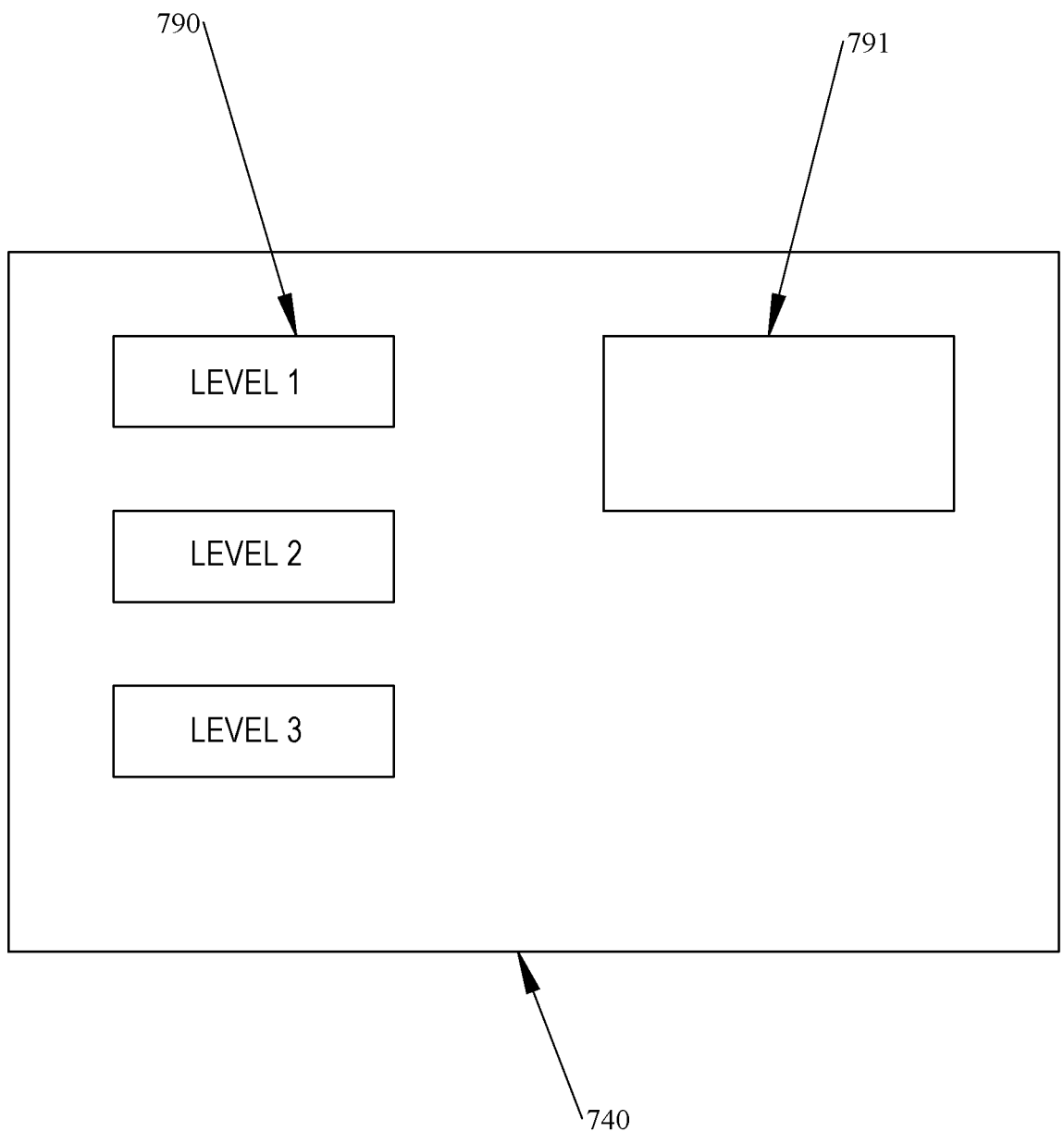
FIG. 7C is schematic diagram of a user interface in accordance with one embodiment of the present disclosure showing multiple choices for a user to set a cycle to clean, disinfect and/or sterilize multiple medical devices of choice.

FIG. 7C shows one example user interface 740, where a user has three options for cleaning, disinfecting, and sterilizing cycles. In accordance with this embodiment, the device and system has preset parameters for critical, semi-critical and non-critical devices, as listed in the background, and the user can initiate the appropriate cycle level 790, shown as level 1, level 2 and level 3, based on the medical device, medical device tube, adapters and guidelines available to the user for choosing the correct cycle for each medical device. In accordance with this embodiment, the user interface 740 may display in a display window 791 cycle time, specific level information such as ozone gas levels, UV light requirements, time of cycle, repeat schedules, error signals and the like.

In accordance with the embodiment shown in FIGS. 7A-7C a user manual may be provided with required cycle levels and ozone treatment levels for treating a medical device, such as critical, semi-critical and non-critical devices, and any other medical devices and passageways and devices with tubes not listed herein. In accordance with this example, the user manual may associate the required cycle level and/or ozone treatment level with a list of specific devices, a list of specific adapters to connect to the ozone ports for each device to be treated in a cleaning, disinfecting and/or sterilization cycle and the ultraviolet light cycle for devices listed in each level, for ease of review and ease of preparation of a device for treatment with the multi-channel ozone treatment device in accordance with an embodiment of the present invention.

Figure 8:
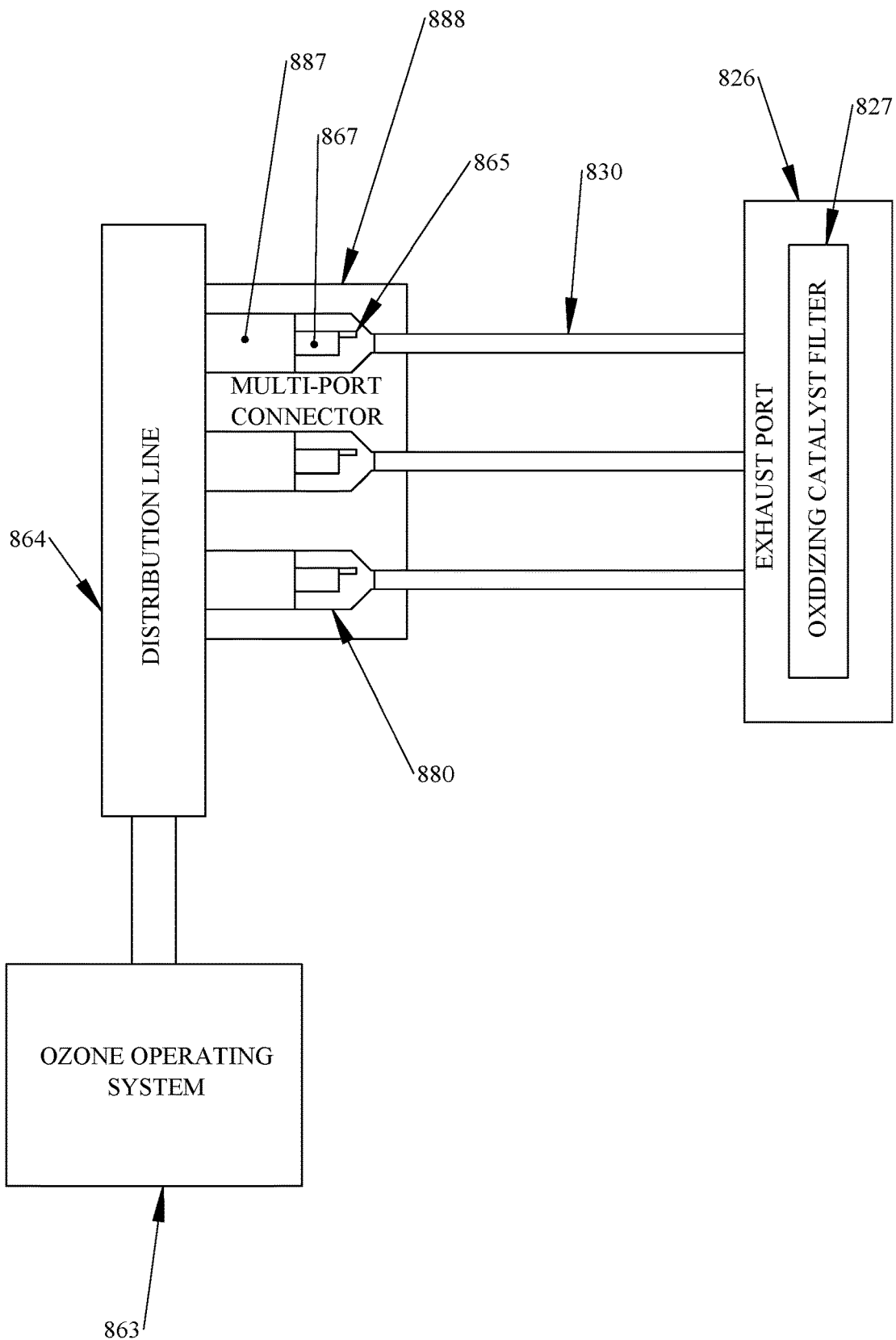
FIG. 8 is a schematic diagram of a multi-channel ozone treatment system including a multi-port connector unit connected to medical device tubes in accordance with an embodiment of the present disclosure.

FIG. 8 shows a multi-port connector unit 888 connected to an ozone operating system 863 through a distribution line 864, with a plurality of distribution channels 887 distributing ozone into the medical device tubes 830. In accordance with this embodiment, the multi-port connector unit 888 has three connector units 880 extending from the body of the multi-port connector unit 888. In this embodiment the connector units 880 may connect directly to the distribution channels 887 or to ozone ports connected to the distal end of the ozone distribution channels 887. In accordance with this embodiment, the multi-port connector unit 888 distributes ozone into three medical device tubes 830 to clean, disinfect and sterilize the medical device tubes 830. A multi-tube exhaust port 826 in this embodiment s coupled to the distal end of the medical device tubes 830. In this embodiment an oxidizing catalyst filter 827 is coupled to the exhaust port 826 for controlled and slow release of ozone $O^3$ as oxygen $O^2$. Further in this embodiment, the distribution channels 887 each have a check valve 867 to prevent ozone from flowing from the medical device tubes back into the distribution line 864. In accordance with this embodiment, the ozone operating system 863 has an ozone generator, an air pump and a fan that pushes the ozone into the desired direction, through the distribution line 864, the plurality of distribution channels 887, the medical tubes 830 and the exhaust port 826, thereby safely and effectively treating the medical device tubes 830. A sensor 865 is provided in this embodiment to detect the ozone levels in the medical device tubes 830 during and after a cycle, confirming that a cycle has reached the required ozone levels, confirming that the medical device tubes 830 are safe for reuse and confirming that the ozone has safely released from the medical device tubes 830 through the exhaust port 826. The sensors 865 in this embodiment may be coupled to the connector units 880, to the multi-port connector unit 888, and be extended into the medical tubes 830 in an embodiment of the present invention.

Figure 9:
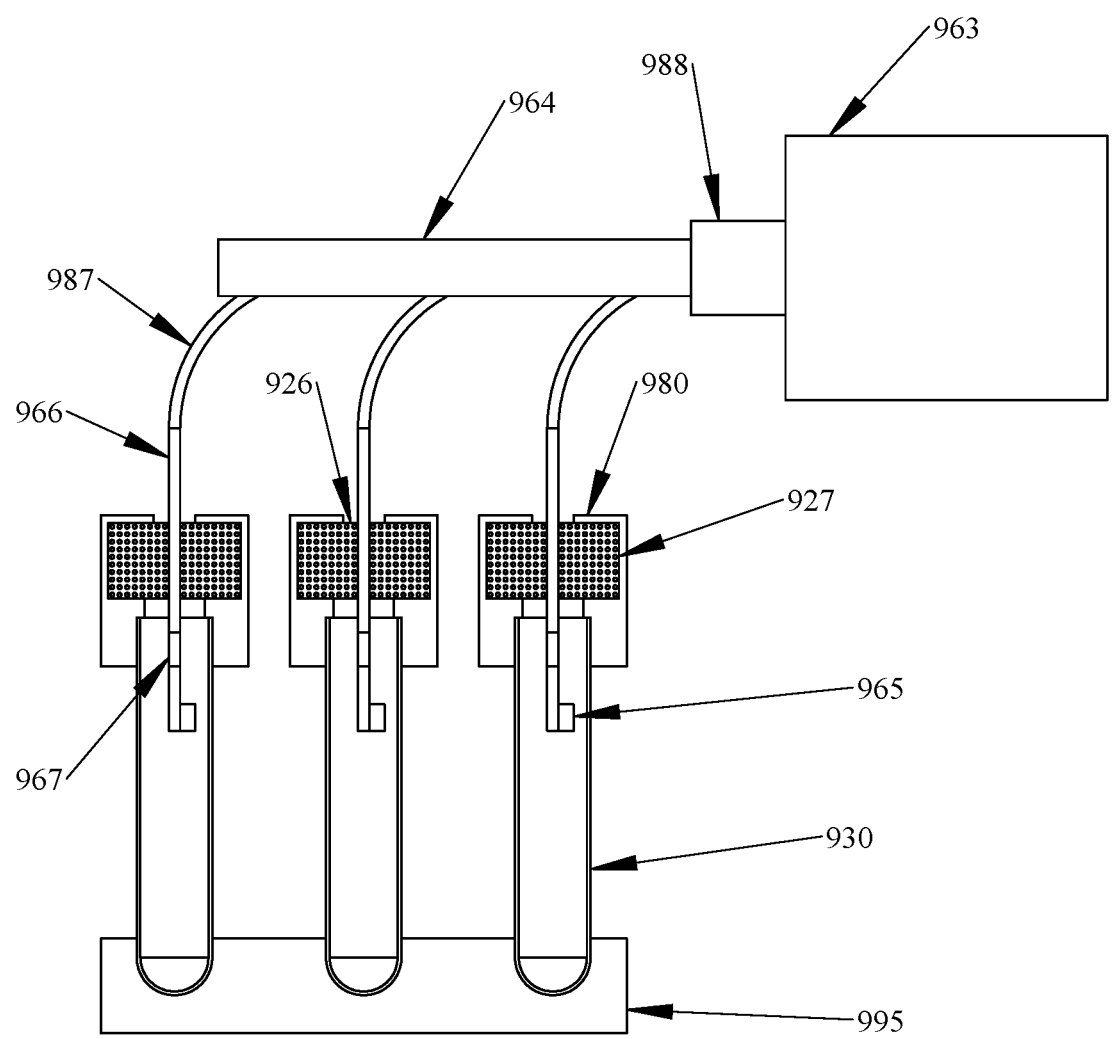
FIG. 9 is a schematic diagram of a multi-line connector unit connected to medical device passageways in accordance with an embodiment of the present disclosure.

The embodiment in FIG. 9 shows devices, systems and methods in accordance with the present invention, of cleaning, disinfecting and/or sterilizing a tube with a closed end in accordance with the present invention. FIG. 9 of the present disclosure, shows a multi-line connector unit 988 connected to an ozone operating system 963 through a distribution line 964, with a plurality of distribution channels 987 distributing ozone into the medical device tubes 930. In accordance with this embodiment the multi-line connector unit 988 has three connector units 980, with an exhaust port 926 with an oxidizing catalyst filter 927 embedded into each connector unit 980, such that one of a plurality of distribution channels 987 traverses through the exhaust port 926 embedded in one connector unit 980 extending from the body of the multi line connector unit 988. In accordance with this embodiment, the plurality of distribution channels 987 distribute ozone to the medical tubes 930 to clean, disinfect and/or sterilize the medical tubes 930 and ozone will release from the medical tubes through the exhaust port 926, as shown in FIG. 9. The exhaust port 926 may further have an oxidizing catalyst filter 927 coupled to the exhaust port 926, and the distribution channels 966 may further have a check valve 967 to prevent back-flow of ozone. In addition, in accordance with this embodiment a sensor 965 is provided on the plurality of distribution channels 987 to sense ozone gas in the medical device tubes 930 and provide the user with cycle and ozone gas information, including but not limited to cycle input and output information, and specific gas levels. Further in accordance with this embodiment a tube holder 995 can be used to hold the tubes in place during a treatment cycle.

Thus, in accordance with the embodiment in reference to FIG. 9, a system comprising: an ozone operating system connected to a plurality of channels for distributing ozone; a multi-line connector unit, wherein the multi-line connector unit comprises two or more connector units attached and fluidly connected to the proximal end of two or more medical device tubes; and, an exhaust port on the two or more connector units of the multi-port connector unit, wherein one of the plurality of channels traverses the exhaust port into each medical device tube, thereby dispersing ozone gas into the medical device tube, and whereby ozone is released from the medical device tube through the exhaust port connected at the proximal end of the medical device tube, is further described herein. In accordance with this embodiment the system may further comprise a check valve in the plurality of channels and a fan in the ozone operating system that pushes ozone into the medical device tubes. In yet further embodiments, a single medical tube, bottle or other compartment with a closed end on one side can be cleaned, disinfected and/or sterilized with the embodiment disclosed in accordance with the present disclosure.

The systems, methods and devices of the present disclosure will have a series of user displays, timers and safety measures for safe operation of the embodiments. In one embodiment, for example, once a user loads the medical devices to be cleaned, disinfected and/or sterilized, and presses the turn on power switch, the following steps occur: the time needed for the unit to run will be displayed on a user interface to a user; a check is made to determine if the locking mechanism is engaged; and if it is not engaged, the user interface will not be accessible for a user to proceed with a cycle using an on/off type button. Other warning signals that will be prompted to a user for safe operation of the device in accordance with one or more embodiments of the present disclosure include a warning signal if the device does not detect current coming from the air pump, if the unit does not detect current coming from the ozone tube, and/or if the unit does not detect current coming from the UV lights, and if the ozone gas levels do not reach the required level according to the cycle criteria. A user will have an option of having a UV light turn on during a cycle, if the user selects the UV display option, the cycle run time will increase to accommodate the additional UV cycle, increasing a cycle time by about five minutes, and in other embodiments about 10 seconds to 15 minutes.

In one embodiment of the present disclosure, once the start button is pressed and the device signals all clear for starting a process, a user can press or preselect a start time for a cleaning, disinfecting and/or sterilizing cycle to begin to treat multiple medical devices and multiple medical device tubes. Once a cycle is initiated, the ozone generator is turned on and the air pump is turned on. After a select time period, the ozone generator, and air pump are turned off and the air pump is turned on again after a few minutes to remove residual ozone in the ozone tubing. If a UV cycle has been selected, the UVC light will be turned on for about 5 minutes, and once the UVC light is turned off, the air pump will be turned on again for an additional 1 minute cycle to remove any ozone remaining in the gas-tight compartment, through the exhaust ports. At the completion of the cycle, a sound buzzer is activated and a notification, such as an LED light is displayed to indicate that the cycle has been completed. Once a cycle has been completed, the device is prepared for a user to initiate a new cycle.

Thus, in accordance with an embodiment of the present disclosure of the present a system having a device and a gas-tight compartment is described, wherein the system comprises: a plurality of ozone distribution channels coupled to a plurality of ozone ports in the gas compartment; two or more medical device tubes attached at the proximal end of an ozone port, and, an exhaust port for releasing ozone from the gas-tight compartment and safety measures for sensing and controlling the ozone input and output and control mechanisms for assuring ozone is released from medical tubes are disclosed herein. A UV light may also be provided in the gas-tight compartment as an optional additional treatment system. Further a magnesium oxide filter coupled to the exhaust port for managing safe release of ozone into the ambient environment is further disclosed.

In yet other embodiments, a plurality of distribution channels connected to two or more ozone ports and a multi-port connector is described, wherein the multi-port connector unit comprises, two or more connector units attached and fluidly connected at a proximal end to the two or more ozone ports; a distal end fluidly connected to the proximal end of two or more medical device tubes, wherein the distal end converts the size and/or shape of the ozone ports to release ozone into a medical device tube sized and shaped to securely connect at a proximal end to the distal end of the two or more connector units; and, a gas-tight compartment encasing the multi-port connector unit, the ozone ports and the medical device tubes. The multi-port connector unit in accordance with this embodiment further comprising an exhaust port on the gas-tight compartment and an oxidizing catalyst coupled to the exhaust port.

In yet another embodiment a system comprising an ozone operating system connected to a plurality of channels for distributing ozone; a multi-line connector unit, wherein the multi-line connector unit comprises, two or more connector units attached and fluidly connected each at a proximal end to one of the plurality of channels; a distal end connected to the proximal end of two or more medical device tubes; and, a multi-tube receiving exhaust port connected to the distal end of the medical device tubes is described. The system may further comprise a check-valve on each of the plurality of distribution channels, a filter coupled to the exhaust port, a sensor for sensing ozone input and output in the medical device tubes and a user interface for displaying cleaning, disinfection and sterilizing cycle information, including ozone input and output information.

It should be emphasized that the above-described embodiments of the present disclosure, particularly, any "preferred" embodiments, are merely possible examples of implementations, merely set forth for a clear understanding of the principles of the disclosure. Many variations and modifications may be made to the above-described embodiments of the disclosure without departing substantially from the spirit and principles of the disclosure. All such modifications and variations are intended to be included herein within the scope of this disclosure and protected by the following claims.

What is claimed is:

1. A system for treating components of a continuous positive airway pressure (CPAP) device, comprising:
   a CPAP hose;
   a CPAP mask;
   an ozone operating system configured to generate ozone gas;
   a container comprising a plurality of walls, wherein a first wall of the plurality of walls is configured to move such that the container can transition between an open position and a closed position, the container comprising an interior that is configured to receive at least the CPAP mask therein;
   an exhaust port on the first wall;
   an oxidizing catalyst for converting ozone to oxygen, the oxidizing catalyst coupled to the exhaust port on the first wall such that the oxidizing catalyst is movable with the first wall; and
   an ozone port extending through a second wall of the plurality of walls of the container, such that a first end of the ozone port is disposed outside the container and a second end of the ozone port is disposed within the interior of the container;
   wherein:
   the ozone operating system is configured to fluidly couple to the first end of the ozone port and the second end of the ozone port is configured to fluidly couple to a first end of the CPAP hose, such that in operation, ozone gas generated by the ozone operating system flows into the first end of the ozone port, out of the second end of the ozone port, into an interior of the CPAP hose, out of the CPAP hose into the interior of the container, and through the exhaust port and the oxidizing catalyst.

2. The system of claim 1, wherein said CPAP hose comprises a second end configured to couple to the CPAP mask.

3. The system of claim 1, wherein the oxidizing catalyst is disposed within the exhaust port.

4. The system of claim 1, wherein the interior of the container is sized and configured to receive at least a water reservoir of a CPAP machine and the CPAP mask at the same time.

5. The system of claim 1, wherein the ozone operating system comprises an ozone generator.

6. The system of claim 1, wherein the system further comprises an indicator to at least indicate when a sanitizing cycle is complete.

7. The system of claim 6, further comprising a sensor to sense a detected ozone concentration within the interior of said container.

8. The system of claim 7, wherein said indicator is to indicate that a sanitizing cycle is complete when a detected ozone concentration within the interior of said container is below a threshold level.

9. The system of claim 1, further comprising a pump to facilitate a flow of ozone gas from said ozone operating system to an interior of said container.

* * * * *